United States Patent
Malik et al.

(10) Patent No.: US 6,723,688 B1
(45) Date of Patent: Apr. 20, 2004

(54) CLEANSER THAT IS GENTLE TO HUMAN SKIN

(75) Inventors: Arshad H. Malik, Dublin, CA (US); Mukhtar Siddiqui, San Ramon, CA (US); Yoshi Kawasaki, San Francisco, CA (US)

(73) Assignee: Shaklee Corporation, Pleasonton, CA (US)

(*) Notice: Subject to any disclaimer, the term of this patent is extended or adjusted under 35 U.S.C. 154(b) by 67 days.

(21) Appl. No.: 10/070,404

(22) PCT Filed: Sep. 26, 2000

(86) PCT No.: PCT/US00/41002
§ 371 (c)(1),
(2), (4) Date: Jul. 12, 2002

(87) PCT Pub. No.: WO01/23517
PCT Pub. Date: Apr. 5, 2001

Related U.S. Application Data

(60) Provisional application No. 60/156,137, filed on Sep. 27, 1999.

(51) Int. Cl.$^7$ ................................................ A61K 7/50
(52) U.S. Cl. .................. 510/130; 510/155; 510/156; 510/159; 510/424; 510/425; 510/426; 510/428; 510/431; 510/436; 510/470; 510/490; 510/492
(58) Field of Search ................................ 510/130, 155, 510/156, 159, 424, 425, 426, 428, 431, 436, 470, 490, 492; 424/70.1

(56) References Cited

U.S. PATENT DOCUMENTS

| | | | |
|---|---|---|---|
| 4,673,525 A | 6/1987 | Small et al. | |
| 4,812,253 A | 3/1989 | Small et al. | |
| 4,968,450 A | 11/1990 | Kamegai et al. | |
| 5,015,414 A | 5/1991 | Kamegai et al. | |
| 5,073,293 A | 12/1991 | Deguchi et al. | |
| 5,084,212 A | 1/1992 | Farris et al. | |
| 5,096,608 A | 3/1992 | Small et al. | |
| 5,252,246 A | 10/1993 | Ding et al. | |
| 5,322,643 A | 6/1994 | Schwartz et al. | |
| 5,480,633 A | 1/1996 | Simion et al. | |
| 5,562,912 A | 10/1996 | Burke et al. | |
| 5,567,359 A | 10/1996 | Cassidy et al. | |
| 5,632,978 A | 5/1997 | Moore et al. | |
| 5,653,970 A | 8/1997 | Vermeer | |
| 5,663,137 A | 9/1997 | Giesen et al. | |
| 5,683,683 A | 11/1997 | Scafidi | |
| 5,688,752 A | 11/1997 | Turner | |
| 5,785,979 A | 7/1998 | Wells | |
| 5,866,110 A | 2/1999 | Moore et al. | |
| 5,883,068 A | 3/1999 | Hensen et al. | |
| 5,888,951 A | 3/1999 | Gagnebien et al. | |
| 5,908,617 A | 6/1999 | Moore et al. | |
| 5,912,002 A | 6/1999 | Grieveson | |
| 5,928,993 A | 7/1999 | Johansson | |
| 5,932,202 A | 8/1999 | Guskey et al. | |
| 5,985,808 A | * 11/1999 | He et al. ................ | 510/155 |
| 6,126,954 A | 10/2000 | Tsaur | |

* cited by examiner

Primary Examiner—Necholus Ogden
(74) Attorney, Agent, or Firm—Klarquist Sparkman, LLP

(57) ABSTRACT

Compositions for cleansing are disclosed that are not irritating to human skin. A composition is disclosed that includes at least 2% of a mixture of a salt of an alkyl sulfoacetate and a salt of an ethoxylated alkyl sulfosuccinate, at least 3% of a salt of an ethoxylated alkyl sulfate, at least 1% of an amphoteric surfactant, at least 0.05% of an alkyl glucoside, and at least 0.005% of a phospholipid. A composition for cleansing is disclosed that includes about 2% to 70% of a mixture of a salt of an alkyl sulfoacetate and a salt of an ethoxylated alkyl sulfosuccinate, about 3% to 40% of a salt of an ethoxylated alkyl sulfate, about 1% to 40% of an amphoteric surfactant, about 0.05% to 10% of an alkyl glucoside, and about 0.005% to 10% of a phospholipid. A cleansing composition is further disclosed that includes about 41% of a mixture of alkyl sulfoacetate and ethoxylated alkyl sulfosuccinate, about 34% of an ethoxylated alkyl sulfate, about 22% of an amphoteric surfactant, about 2% of a alkyl glucoside, and about 0.5% of a phospholipid. A composition for cleansing is also described which includes about 2% to 50% of a mixture of a salt of a sodium lauryl sulfoacetate and Disodium Laureth Sulfosuccinate, about 3% to 35% of Ammonium Laureth Sulfate, about 1% to 30% of Cocamidopropyl Betaine, about 0.05% to 8% of Coco-Glucoside and Coconut Oil, and about 0.005% to 5% of a phospholipid. A method of cleaning is also described, which includes contacting a surface to be cleansed with the composition of the invention. The composition can be used in a variety of personal care or household cleansers, such as contact lens care products, shampoos, soaps, body washes, mouthwashes, toothpastes, oral rinses, facial and wound cleansers, eye makeup removers, laundry and dishwashing detergents, and others.

56 Claims, No Drawings

this is …

CLEANSER THAT IS GENTLE TO HUMAN SKIN

PRIORITY CLAIM

This is a §371 U.S. national stage of PCT/US00/41002, filed Sep. 26, 2000, which was published in English under PCT Article 21(2), and claims the benefit of U.S. application Ser. No. 60/156,137, filed Sep. 27, 1999.

FIELD OF THE INVENTION

This invention relates to methods and preparations for cleansing, specifically to methods and compositions that do not irritate the skin.

BACKGROUND OF THE INVENTION

Cleansing products come in many types and forms, but are generally divided into personal care cleansers and household cleansers. The personal care cleansers most commonly thought of by consumers are skin cleansers (including bar soaps) and shampoos. However, this class of product also includes body washes, personal hygiene cleansers, contact lens cleansers, dental cleansers, facial cleansers, and makeup removers (including eye makeup removers). The general class of household cleansers includes laundry detergents, hard surface cleansers, porous surface cleansers, dishwashing detergents, window cleansers, scouring cleansers and disinfectant cleansers. Although each of these products contains a specific set of specialized ingredients depending upon the particular end use of the product, they all contain surfactants.

The most common type of cleansing product is a liquid or a powder formulation. However, cleansing products can also be in such forms as an aerosol, a mousse, a gel, an emulsion, a discrete packet, or impregnated on a towelette. Although these cleansers come in many different forms, they all have in common the presence of a surfactant.

In view of their ubiquitous use, surfactants in cleansing products often come into contact with human skin. Although this contact may be brief or even secondary (as for instance clothing washed with laundry detergent), it is desirable that cleansing products have a minimal dermatologic effect. Unfortunately, surfactants often cause irritation, dryness, cracking and peeling of the skin. Additionally, there are known case reports in the dermatological literature documenting allergic dermatitis in response to contact with a cleansing product. The allergic reaction can be caused by the fragrance contained in the cleansing product, or by the surfactant itself. In general, if a surfactant system can be applied directly to human skin without causing irritation, it will be safe for use in products used to cleanse materials that contact the skin (such as laundry detergent), or in products with limited direct contact with the skin (such as household products, including hard surface cleansers, window cleansers, and automotive cleansers).

Numerous patents have issued which concern cleansing products that include surfactants, and mixtures of surfactants, which are designed to be mild to the skin (e.g., U.S. Pat. No. 5,908,617; U.S. Pat. No. 5,785,979; U.S. Pat. No. 5,663,137; U.S. Pat. No. 5,632,978; U.S. Pat. No. 5,567,359; U.S. Pat. No. 5,562,912; U.S. Pat. No. 5,480,633; U.S. Pat. No. 5,322,643; U.S. Pat. No. 5,252,246; U.S. Pat. No. 5,096,608; U.S. Pat. No. 5,084,212; U.S. Pat. No. 5,073,293; U.S. Pat. No. 5,015,414; U.S. Pat. No. 4,968,450; U.S. Pat. No. 4,812,253; U.S. Pat. No. 4,673,525). However, each of these formulations has limitations. These limitations include limited foam volume, an undesired skin feel of the foam, instability, etc. that require the addition of other agents, some of which are not commercially available. Thus there is a need for a surfactant composition that is mild to the skin and eyes and can be easily produced.

SUMMARY OF THE INVENTION

A surfactant composition has been discovered that is mild to the skin, leaves the skin barrier intact, is stable, can be formulated into any type of cleansing preparation, and uses commonly available surfactants. In addition to being gentle to the skin, the surfactant composition is extremely mild to eye tissue, and is therefore suitable for contact lens solutions or other cleansers (such as shampoos) that contact the eye. The surfactant composition has a stable viscosity and an acceptable skin feel without the addition of polymeric materials.

A composition for cleansing is disclosed. The composition includes at least about 2% of a mixture of a salt of an alkyl sulfoacetate and a salt of an ethoxylated alkyl sulfosuccinate, at least about 3% of a salt of an ethoxylated alkyl sulfate, at least about 1% of an amphoteric surfactant, at least about 0.05% of an alkyl glucoside, and at least about 0.005% of a phospholipid.

A cleansing composition is also disclosed that includes about 2% to about 70% of a mixture of a salt of an alkyl sulfoacetate and a salt of an ethoxylated alkyl sulfosuccinate, about 3% to about 40% of a salt of an ethoxylated alkyl sulfate, about 1% to about 40% of an amphoteric surfactant, about 0.05% to about 10% of an alkyl glucoside, and about 0.005% to about 10% of a phospholipid.

In addition, a cleansing composition is disclosed that includes about 41% of a mixture of alkyl sulfoacetate and ethoxylated alkyl sulfosuccinate, about 34% of an ethoxylated alkyl sulfate, about 22% of an amphoteric surfactant, about 2% of an alkyl glucoside, and about 0.5% of a phospholipid.

A method of cleaning, including contacting a surface to be cleansed with a composition of the invention, is also described. The invention also includes cleansing compositions to which the surfactant has been added.

The foregoing and other objects, features, and advantages of the invention will become more apparent from the following detailed description of particular embodiments.

DETAILED DESCRIPTION OF SEVERAL EMBODIMENTS

Compositions including a combination of surfactants have been found that are very mild (gentle) to the skin and eye tissues such that they cause minimal, if any, irritation of these tissues. Although materials contained in the compositions are generally recognized as safe, the combination causes less irritation to the tissues than would be expected based on the irritation caused by the components individually. The compositions do not require the presence of any known anti-irritant compounds to achieve the level of safety found.

The compositions are unique for several additional reasons. They do not require the presence of ancillary materials to achieve levels of foam generally desired by consumers, and do not require the presence of polymeric materials to achieve a stable viscosity or skin feel often desired by consumers. Moreover, the compositions do not require the presence of solubilizers and stabilizers to achieve a suitable product shelf life, even when stored at the extremes of temperature, such as high temperatures (as high as 50° C.) or low temperatures (less than 4° C.). This combination of effects is both unexpected and unique among surfactants.

DEFINITIONS

The terms "a" and "the" include the plural as well as the singular, unless the context clearly indicates otherwise.

The term "surfactant" refers to a surface-active agent that reduces surface tension when dissolved in water or an aqueous solution, or which reduces interfacial tension between two liquids, or between a liquid and a solid. Detergents, wetting agents and emulsifiers are examples of surfactants.

An "amphoteric" surfactant refers to a surfactant that has the capacity of behaving either as an acid or a base. Specific, non-limiting examples of an amphoteric surfactant are betaine, sultaine, hydroxysultaine, imidazoline, aminoalkanoate, and iminoalkanoate surfactants.

The term "phospholipid" refers to a lipid compound that yields on hydrolysis phosphoric acid, an alcohol, a fatty acid, and a nitrogenous base. Phospholipids include, but are not limited to, Coco Phosphatidyl PG-Dimonium Chloride, Linoleamidopropyl Phosphatidyl PG-Dimonium Chloride, Cocamidopropyl Phosphatidyl PG-Dimonium Chloride, Borageamidopropyl Phosphatidyl PG-Dimonium Chloride, Stearamidopropyl Phosphatidyl PG-Dimonium Chloride, lecithin, and derivatives of lecithin.

The term "alkyl" refers to a cyclic, branched, or straight chain alkyl group containing only carbon and hydrogen, and unless otherwise mentioned contains one to thirty carbon atoms. This term is further exemplified by groups such as methyl, ethyl, n-propyl, isobutyl, t-butyl, pentyl, hexyl, heptyl, adamantyl, and cyclopentyl. Alkyl groups can either be unsubstituted or substituted with one or more substituents, e.g. halogen, alkyl, alkoxy, alkylthio, trifluoromethyl, acyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to seven carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, hexyl and heptyl. Lower alkyl groups can also be unsubstituted or substituted. The term "higher alkyl" refers to a cyclic, branched or straight chain monovalent alkyl radical of eight to thirty carbon atoms. Higher alkyl groups can also be unsubstituted or substituted.

The term "glycoside" refers to an organic compound which can be reduced by hydrolysis into sugars and other organic substances, known as glycones. The term "glucoside" refers to a glycoside which has glucose as the sugar constituent. An "alkyl glucoside" includes the linear or branched chain alcohols, including but not limited to those from coconut oils, palm oils, etc. or mixtures thereof.

"Hydroxyl" refers to —OH.

"Alcohol" refers to R-OH, wherein R is alkyl, especially lower alkyl (for example in methyl, ethyl or propyl alcohol), but can also be a higher alcohol (for example decyl or dodecyl). An alcohol may be either linear or branched, such as isopropyl alcohol.

"Carboxyl" refers to the radical —COOH, and substituted carboxyl refers to —COOR where R is alkyl, lower alkyl or a carboxylic acid or ester.

"Salt" refers to the compound formed when the hydrogen of an acid is replaced by a metal or its equivalent (e.g., an $NH_4$ radical). The salts include the monovalent ions (lithium, sodium and potassium, etc.), the divalent ions (barium, calcium etc.), the trivalent ions (aluminum, etc.), or the ammonium based ions (ammonium, monoalkyl-, dialkyl-, and trialkylammonium ion, such as triethanolammonium ion) or mixtures thereof.

Other chemistry terms herein are used according to conventional usage in the art, as exemplified by *The McGraw-Hill Dictionary of Chemical Terms* (1985) and *The Condensed Chemical Dictionary* (1981).

SEVERAL EXAMPLES OF SURFACTANT COMPOSITION

Combinations of surfactants have been found that are very mild (gentle) to the skin and eye tissues such that they cause minimal, if any, irritation of these tissues. The composition includes least about 2% of a mixture of a salt of an alkyl sulfoacetate and a salt of an ethoxylated alkyl sulfosuccinate, at least about 3% of a salt of an ethoxylated alkyl sulfate, at least about 1% of an amphoteric surfactant, at least about 0.05% of an alkyl glucoside, and at least about 0.005% of a phospholipid. Alternatively, the composition includes least about 15% of a mixture of a salt of an alkyl sulfoacetate and a salt of an ethoxylated alkyl sulfosuccinate, at least about 10% of a salt of an ethoxylated alkyl sulfate, at least about 10% of an amphoteric surfactant, at least about 0.05% of an alkyl glucoside, and at least about 0.05% of a phospholipid.

In one embodiment, the composition includes about 2% to about 70% of a mixture of a salt of an alkyl sulfoacetate and a salt of an ethoxylated alkyl sulfosuccinate, about 3% to about 40% of a salt of an ethoxylated alkyl sulfate, about 1% to about 40% of an amphoteric surfactant, about 0.05% to about 10% of an alkyl glucoside, and about 0.005% to about 10% of a phospholipid. In another embodiment, the composition includes about 15% to about 70% of a mixture of a salt of an alkyl sulfoacetate and a salt of an ethoxylated alkyl sulfosuccinate, about 10% to about 40% of a salt of an ethoxylated alkyl sulfate, about 10% to about 40% of an amphotheric surfactant, about 0.05% to about 10% of an alkyl glucoside, and about 0.05% to about 10% of a phospholipid.

Salts of an alkyl sulfoacetate are well known in the art, and any salt of an alkyl sulfoacetate can be used in the composition. One specific, non-limiting example of a salt of an alkyl sulfoacetate is a salt of a lauryl sulfoacetate. Similarly, salts of an ethoxylated alkyl sulfosuccinate are well known in the art, and any salt of an ethoxylated alkyl sulfosuccinate can be used in the composition. A specific, non-limiting example of a salt of an ethoxylated alkyl sulfosuccinate is a salt of Laureth Sulfosuccinate.

One non-limiting example of a composition that is mild to the skin and eyes is a composition that includes:

| | |
|---|---|
| Salt of Lauryl Sulfoacetate and Salt of Laureth Sulfosuccinate | about 2% to about 70% |
| Salt of Laureth Sulfate | about 3% to about 40% |
| Amphoteric Surfactant | about 1% to about 40% |
| Alkyl Glucoside | about 0.05% to about 10% |
| Phospholipid | about 0.005% to about 10% |

A specific example within this range is:

| | |
|---|---|
| Salt of Lauryl Sulfoacetate and Salt of Laureth Sulfosuccinate | about 15% to about 70% |
| Salt of Laureth Sulfate | about 10% to about 40% |
| Amphoteric Surfactant | about 10% to about 40% |
| Alkyl Glucoside | about 0.05% to about 10% |
| Phospholipid | about 0.05% to about 10% |

Another non-limiting example of a surfactant composition that is mild to the skin and eyes is:

| | |
|---|---|
| Sodium Lauryl Sulfoacetate and Disodium Laureth Sulfosuccinate | 34.90% |
| Ammonium Laureth Sulfate | 34.62% |
| Cocamidopropyl Betaine | 23.08% |
| Coco-Glucoside and Coconut Oil | 6.49% |
| Coco Phosphatidyl PG-Dimonium Chloride | 0.91% |
| Total | 100.00% |

In general, the ratio of the agents included in the surfactant composition that is mild to the skin and eyes is from about 0.05 to about 2.0 of a salt of an ethoxylated alkyl sulfosuccinate, from about 0.05 to about 1.5 of a salt of an alkyl sulfoacetate, from about 0.1 to about 2.0 of a salt of an ethoxylated alkyl sulfate, from about 0.05 to about 3.0 of an amphoteric surfactant, from about 0.005 to about 1.0 of an alkyl glucoside, and from about 0.0005 to about 0.5 of a phospholipid. More specifically, the ratio of agents included in the surfactant composition that is mild to the skin and eyes is from about 0.2 to about 1.5 of a salt of an ethoxylated alkyl sulfosuccinate, from about 0.1 to about 1.0 of a salt of an alkyl sulfoacetate, from about 0.2 to about 1.8 of a salt of a ethoxylated alkyl sulfate, from about 0.05 to about 2.5 of an amphoteric surfactant, from about 0.1 to about 0.7 of a alkyl glucoside, and from about 0.005 to about 0.1 of a phospholipid.

In one embodiment, the ratio of agents included in the surfactant composition is about 0.7 of a salt of an ethoxylated alkyl sulfosuccinate, about 0.3 of a salt of an alkyl sulfoacetate, about 1.0 of a salt of an ethoxylated alkyl sulfate, about 0.7 of an amphoteric surfactant, about 0.2 of a alkyl glucoside, and about 0.02 of a phospholipid (about a 0.7:0.3:1.0:0.7:0.2:0.02 ratio). In another embodiment, the ratio of the salt of an ethoxylated alkyl sulfosuccinate to the salt of an alkyl sulfoacetate is from about 0.7:1 to about 6.6:1 in the surfactant composition that is mild to the skin and eyes. In yet another embodiment, the ratio of the salt of an ethoxylated alkyl sulfosuccinate to the salt of an alkyl sulfoacetate is about 2.3:1.

In general, the ratio of the phospholipid to the other surfactants included in this surfactant composition that is mild to skin and eyes is from to 1:10 to about 1:44 for a salt of an ethoxylated alkyl sulfosuccinate, from about 1:1 to about 1:22 for a salt of an alkyl sulfoacetate, from about 1:15 to about 1:60 for a salt of an ethoxylated alkyl sulfate, from about 1:10 to about 1:40 for an amphoteric surfactant, and from about 1:0.5 to about 1:15 for an alkyl glucoside. More preferably, the ratio of phospholipid to the other surfactants included in this surfactant composition is from about 1:20 to about 1:34 for a salt of an ethoxylated alkyl sulfosuccinate, from about 1:8 to about 1:15 for a salt of an alkyl sulfoacetate, from about 1:25 to about 1:50 for a salt of an ethoxylated alkyl sulfate, from about 1:20 to about 1:30 for an amphoteric surfactant, and from about 1:2 to about 1:12 for an alkyl glucoside. Most preferably, the ratio of phospholipid to the other surfactants included in this surfactant composition is about 1:27 for a salt of an ethoxylated alkyl sulfosuccinate, about 1:12 for a salt of an alkyl sulfoacetate, about 1:38 for a salt of an ethoxylated alkyl sulfate, about 1:25 for an amphoteric surfactant, and about 1:7 for an alkyl glucoside.

The alkyl glucoside can include several agents, such as linear or branched chain alcohols, including but not limited to coconut oils, palm oils, etc. or mixtures thereof. In one embodiment, coconut oil is included in the alkyl glucoside.

A preservative can be included in the surfactant composition. Preservatives are well known to one of skill in the art. Examples of preservatives include, but are not limited to, DMDM Hydantion, Imidazolidinyl Urea, Diazolidinyl Urea, Benzyl Alcohol, Coco Phosphatidyl PG-Dimonium Chloride, Parabens (including methyl-, ethyl-, propyl-, butyl-, isobutyl-, etc.), and Salts of Ethylenediamine Tetraacetate.

The surfactant composition can further include an agent to give opacity and/or pearlescence. Agents that give opacity and pearlescence are well known to one of skill in the art. Specific, non-limiting examples of agents that give opacity and pearlescence are Ethylene Glycol Distearate, Propylene Glycol Distearate Polyoxypropylene Glycol (POP) Distearates, Polyoxyethylene Glycol (POE) Distearates, Polyoxyethylene/Polyoxypropylene (POE/POP) Distearate, any high molecular weight distearates or similar fatty acids (dilaurates, dimyristates, dipalmitates etc.), and mica based pearlescent agents.

A skin feel additive can also be included in the composition. A "skin feel additive" refers to an agent that creates or modifies the feel of a formulation on the skin. Skin feel additives are well known to one of skill in the art. Skin feel additives include, but are not limited to, silicones, taurates, and proteins. In general, any emollient material can be used. In one embodiment, the skin feel additive is an emollient ester, such as Octyl Palmitate, Cetearyl Octonoate. However, any non-water soluble material, even mineral oil could be used for this purpose.

An antioxidant can also be included in the composition. Non-limiting examples of antioxidants of use in the composition include pro-vitamins, vitamins, plant extracts, enzymes, and oat derivatives. One of skill in the art will readily be able to identify an antioxidant of use in a surfactant composition.

The composition can also include specialty ingredients that are designed to provide specialized functions to the composition. Examples of specialty ingredients are salts, colorants (such as pigments, dyes, food grade colors, etc.), vitamins (such as Vitamin C as an antioxidant), enzymes, alpha- or beta-hydroxy acids (to improve skin appearance), and plant-derived or animal-derived materials, including plant or animal extracts. One of skill in the art can readily identify specialty ingredients of use in a surfactant composition.

The cleansing composition can be introduced into an end product, such as a shower gel, shampoo, or contact lens solution. Such preparations would contain from about 2% to about 50% of a mixture of a salt of a sodium lauryl sulfoacetate and Disodium Laureth Sulfosuccinate, from about 3% to about 35% of Ammonium Laureth Sulfate, from about 1% to about 30% of Cocamidopropyl Betaine, from about 0.05% to about 8% of Coco-Glucoside and Coconut Oil, and from 0.005% to about 5% of a phospholipid. In one embodiment, such preparations would contain from about 5% to about 40% of a mixture of a salt of a sodium lauryl sulfoacetate and Disodium Laureth Sulfosuccinate, from about 5% to about 30% of Ammonium Laureth Sulfate, from about 3% to about 20% of Cocamidopropyl Betaine, from about 0.5% to about 5% of Coco-Glucoside and Coconut Oil, and from 0.05% to about 3% of a phospholipid. One formulation containing the surfactant composition is the following liquid shower gel formulation:

| Ingredients | Percentage (w/w) | |
|---|---|---|
| | General Formula | Specific Formula |
| Sodium Lauryl Sulfoacetate and Disodium Laureth Sulfosuccinate | 29.00 | 29.0000 |
| Water | 39.15 | 25.4846 |
| Ammonium Laureth Sulfate | 24.00 | 24.0000 |
| Cocamidopropyl Betaine | 16.00 | 16.0000 |
| Coco-Glucoside and Coconut Oil | 1.35 | 1.3500 |
| Coco Phosphatidyl PG-Dimonium Chloride | 0.50 | 0.5000 |
| Preservatives | q.s. | 2.1000 |
| Ethylene Glycol Distearate | 0.50 | 0.5000 |
| Fragrance | 0.45 | 0.4500 |
| Skin Feel Additives | — | 0.3000 |
| Antioxidants | — | 0.6054 |
| Specialty Ingredients | — | 0.2100 |
| Total | 100.00 | 100.0000 |

In general, the composition of the invention is a surfactant composition that serves as a concentrate. The concentrated surfactant composition is then diluted in a diluent for use in cleansing. Depending upon the type of product desired, the surfactant composition is incorporated as from about 0.5 to about 90% of the final formulation used for cleansing. Diluents are well known to one of skill in the art. Specific, non-limiting examples of diluents of use are water, solvents such as the lower alkyl alcohols (methyl, ethyl, propyl, isopropyl, butyl, etc.), or a mixture of water and a lower alkyl alcohol.

The compositions can be used in almost any conceivable type of personal care or household product that comes into contact with the skin. The product may be either a prescription product (such as a contact lens care product) or an over-the-counter drug product (such as a shampoo). Non-limiting examples of products include shampoos, soaps, body washes, mouthwashes, toothpastes, oral rinses, personal hygiene products, facial scrubs, facial cleansers, wound cleansers, contact lens cleansers, eye makeup removers, laundry cleaners, dishwashing detergents, hard surface cleaners, disinfectant cleanser, porous surface cleanser, and window cleanser. The composition can be used to clean any surface of interest, by contacting the surface with a sufficient amount of the composition of the invention with a surface to be cleaned. Thus surfaces such as a hard surface, a porous surface, a skin surface, a hair, a fabric or a mucous membrane can be cleansed using a composition of the invention.

Example 1

Evaluation of Surfactant Mixtures for Irritation Potential with Patch Test

The lack of potential for the surfactant compositions of the invention to produce irritation was evaluated by three separate techniques. The first was by a 21 day cumulative irritation test under an occlusive patch followed by a rechallenge test to assess the potential to elicit allergic sensitization reactions. The second method was by evaluating the potential to elicit ocular irritation in cell culture. The final method was the lack of the potential of this surfactant mixture to elicit irritation as assessed by use with human subjects. All of these tests clearly showed an absence of irritation for the surfactant composition. In all of these assay systems, including the user test, there was no significant irritation to any subject, cell or tissue as compared to the controls.

Insult Patch Test

A 21-day repeat insult patch test with rechallenge was conducted at an outside laboratory under the supervision of a certified toxicologist and a board-certified dermatologist. This test involved the application of approximately 0.2 g of a 0.5% composition formulated into a liquid shower gel formulation under a Parke-Davis Readi-Bandage occlusive patch. The patch was applied for a 24 hour period every Monday and Wednesday and for 48 hours every Friday for a three week period (a total of nine patch applications). The skin test site was allowed to rest for 24 hours before the application of each subsequent patch. Prior to the application of each occlusive patch, the skin was graded by a trained observer according to the following 6-point scale:

0=No evidence of any effect

+=Barely perceptible Erythema (Minimal, faint, uniform or spotty)

1=Mild Erythema (Pink, uniform covering moist of the contact site)

2=Moderate Erythema (Pink-red, uniform in the entire site)

3=Moderate Erythema (Bright red, with/without petechiae or papules)

4=Severe Erythema (Deep red, with/without vesiculaton or weeping)

In addition to rating the irritation observed, any other changes in the skin were noted and recorded such as edema, dryness, hypo- and hyper-pigmentation, etc. These other changes were also rated as either mild, moderate or severe.

Results

Based upon this scale, the following results were found for each evaluation point:

| | Irritation Scores | |
|---|---|---|
| Patch Number | + | 1 |
| 1 | 2 | 0 |
| 2 | 1 | 0 |
| 3 | 1 | 0 |
| 4 | 1 | 0 |
| 5 | 1 | 0 |
| 6 | 1 | 0 |
| 7 | 0 | 1 |
| 8 | 1 | 1 |
| 9 | 2 | 0 |

Following a two-week rest, the test formulation was applied again under an occlusive patch to a virgin test site for 24 hours and graded immediately after removal of the patch and at 72 hours following patch removal. This portion of the test evaluated the allergic sensitization potential of the test material. No evidence was found for any allergic potential from the surfactant composition of the invention.

Generally, surfactant solutions elicit a significant number of grade 1 reactions in up to 50% of the panelists, grade 2 reactions in up to 15 to 20% of the panelists, and grade 3 reactions in as many as 2 to 5% of the panelists. Thus the irritation scores obtained with a surfactant composition of the present invention are extremely low. This is highly unusual for a surfactant solution, even a 0.5% solution, applied repeatedly to the same site under occlusion. These values clearly show that the surfactant composition is extremely mild and gentle to the skin.

Example 2

Bovine Ocular Opacity and Permeability Assay

A surfactant composition of the invention was also shown to be mild to the eye using a test for opacity and permeability.

The Bovine Ocular Opacity and Permeability Assay

The Bovine Ocular Opacity and Permeability Assay was conducted on bovine corneas from eyes freshly collected in a local abattoir and evaluated by two end-points: opacity and permeability. The objective values obtained from both parameters were used to calculate the in vitro score. Based on a previously established scale, irritation was classified into three broad categories: mild, moderate and severe.

Bovine eyes were collected in an appropriate container containing Hank's Balanced Salt Solution (HBSS) at a pH of 7.4±0.3. Medium storage and transportation of eyes to the laboratory was performed at room temperature. The eyes were used within two (2) hours of collection.

All eyes were carefully examined, with a stereomicroscope if necessary. Eyes presenting any defects, such as neovascularization, pigmentation, opacity, or scratches were discarded. Selected corneas were dissected with a 2–3 mm rim of sclera for easier handling and stored in a container with HBSS until use. The iris and lens was removed, and the corneas were mounted in holders, with the endothelial side applied on the O-ring of the posterior part of the holder. The anterior part of the holder was placed against the epithelial side of the cornea and held in place with three screws. The holder compartments were then filled, posterior compartment first, with pre-warmed Eagle's Minimum Essential Media with 1% FBS (EMEMF) at a pH of 7.5±0.3 (approximately 32±2° C.). The corneas were then incubated for approximately one hour in a water bath at approximately 32±2° C. to allow pre-equilibration of the corneas to the external medium.

During the pre-equilibration period, the opacitometer was calibrated with no cornea using the calibration set. The electrical zero (balance between photocells) was adjusted to "0" with the balance knob, and the apparatus was then set to "75" with a standard opaque sheet of polyester placed in the "positive" compartment.

After the corneas pre-equilibrated for approximately one hour, both chambers of the holder cassettes were aspirated (anterior compartment first) and refilled with EMEMF (posterior compartment first). Initial opacities were then read (initial corneal opacities had to be low (±0.03) to be included in the study; corneas with higher initial opacities were not used), and the corneas with the lowest opacity scores were selected as negative controls. The EMEMF was removed from the anterior compartment, and the anterior compartment was then dosed with the test material or control as follows:

Liquids—A volume of 0.750 ml of test material or control (pre-warmed to approximately 32±2° C.) was pipetted into the anterior compartment. The test material was distributed uniformly on the corneal surface by rotating the holder with the cornea maintained in a vertical position (holes are plugged with caps). The corneas were then incubated in a vertical position for 10 minutes at approximately 32±2° C. in a water bath. The corneas were timed individually with one cornea being dosed and added to the water bath at regular intervals. After incubation, the test material was removed, and the epithelium was washed at least three times (until the medium is clear) with EMEMF. All of the corneas were collected and the anterior compartment refilled with EMEMF. The corneas were then incubated for approximately 2 hours at approximately 32±2° C. in a water bath. After incubation, the posterior and anterior compartments of the holder were refilled with fresh EMEMF and the corneal opacity was again measured.

Solids—A 20% (w/w) suspension of the solid test in saline was prepared. A volume of 0.750 ml of this suspension was pipetted into the anterior compartment as mentioned for liquid samples above. The procedure listed above for liquids was then followed exactly except for the fact that the samples were incubated with the suspension of the test sample for 4 hours instead of 10 minutes at approximately 32±2° C.

Controls—A positive control was included in each group of products tested. A 5% (w/w) solution of Benzalkonium chloride (BAC) in saline was employed as the control for all liquid and surfactants-containing test samples. A 20% suspension of Imidazole in saline was employed for all non-surfactant-containing solid test samples. The appropriate control was treated the same as the test samples in the procedure listed above. A negative control, saline solution, was also run with each set of corneas tested.

The opacity of the corneas treated with the test samples and control samples were measured by placing the cornea holders, in turn, in the "positive" compartment of the opacitometer while leaving the "negative" compartment empty. The values displayed were recorded. The glass portion of each holder was dried prior to each opacity measurement.

Permeability of the corneas was determined as follows: The EMEMF is removed from the anterior chamber of each holder/cassette. A stock solution of fluorescein was prepared at 4–5% in Dubelcco's Phosphate Buffered Saline (DPBS) at pH 7.5±0.3, and diluted to 0.4–0.5% in EMEMF. One (1) milliliter of the 0.4–0.5% fluorescein solution was added to the anterior compartment and the corneas were incubated in a vertical position in a water bath for approximately 90 minutes at approximately 32±2° C. A 200 microliter portion of media from the posterior compartment of each holder/cassette was removed and its optical density was measured spectrophotometrically at 490 nm in a plate-reader against 200 microliters of EMEMF as a blank.

Five corneas were evaluated for each test sample and control. The opacity of each cornea tested was measured in triplicate (test samples and control samples). The Delta Opacity (DO) values were calculated for each cornea by adjusting for the initial opacity measurement. A mean DO value was then calculated from the DO values for each of the five corneas tested. Each mean DO was then corrected using the mean DO values for the negative control (saline solution) to obtain the mean opacity optical density (MOOD). The permeability value was then determined from the optical density of the EMEMF-containing-fluorescein sample for each treated cornea and then corrected using the mean value recorded for the negative control (saline solution) treated corneas. The corrected mean optical density (MPOD) of each test product and positive control was then calculated.

The in-vitro score for each test product and positive control was calculated according to the following formula:

In-Vitro Score=$MOOD+(15\times MPOD)$

The rating of ocular irritation potential of each material tested was determined according to the following scale:

| In-Vitro Score | Rating |
| --- | --- |
| 0.0 to 5.0 | Non-Irritant |
| 5.0 to 25.0 | Mild Irritant |
| 25.1 to 55.0 | Moderate Irritant |
| 55.1 and above | Severe Irritant |

Results

The results of the Bovine Ocular Opacity assay revealed that the surfactant composition contained in the shower gel formulation was a non-irritant when tested both as a 0.5 and 1% solution in distilled water. In fact, the in-vitro scores of −0.07 for the 0.5% solution and −0.95 for the 1% solution of the surfactant composition contained in the shower gel formulation were not different from the value of 0.00 obtained for distilled water.

Example 3

Gentleness/Mildness of the Surfactant Composition on Intact Human Skin

In addition to testing this surfactant composition for safety, the composition contained in a shower gel formulation was tested on intact human skin for its effect on the skin's barrier properties by determining the effect of the surfactant composition on the capacitance of the skin. The surfactant composition was shown to be mild upon application to human skin.

Measurement of the Moisture Content of Human Skin

The effect of surfactant compositions on the moisture content of the skin was measured using an instrument that measures the capacitance of the skin, namely a Nova™Meter. The capacitance of the skin is directly related to its moisture content. The moisture content of the skin was measured on the skin prior to the application of the test products. A specific amount of a 10% solution of each of the test products was then applied to separate skin sites on a group of six (6) subjects. The test products were allowed to remain in contact with the skin for a specific period of time and then rinsed off the skin using warm distilled water. The control site was only treated with the warm distilled water rinse. Skin moisture measurements were subsequently measured at 0.5, 1, 2, 4, 6 and 24 hours.

Results

The results of the Nova™Meter readings of each of the test sites are shown below (Table 1). The formulation for a shower gel product was compared to a 10% solution of Sodium Lauryl Sulfate (SLS). SLS is a common surfactant used in skin and hair cleansing preparations.

TABLE 1

Measurement of Moisture Content of the Skin

| Time of Evaluation (Hrs.) | Experimental Shower Gel | Solution of SLS | Untreated Site |
| --- | --- | --- | --- |
| 0.0 | 215 | 214 | 213 |
| 0.5 | 191 | 178 | 200 |
| 1.0 | 188 | 165 | 201 |
| 2.0 | 202 | 175 | 207 |
| 4.0 | 211 | 193 | 214 |
| 6.0 | 218 | 210 | 217 |
| 24.0 | 217 | 215 | 216 |

When evaluated using a matched pairs statistical comparison and a 95% confidence limit, the skin treated with the shower gel formulation made from a surfactant composition of the invention was statistically less moist than that of the untreated sites at 0.5, 1, 2, and 4 hours only. The values for the SLS solution treated skin were statistically less moist than that of the untreated site at 0.5, 1, 2, 4, and 6 hours. However, the skin treated with the shower gel formulation made from a surfactant composition of the invention was statistically more moist than those treated with SLS at every evaluation point except for the initial reading (before the application of the test materials). It is also apparent (given the values shown in Table 1) that the skin treated with the shower gel formulation made from a surfactant composition of the invention returned to normal readings much more rapidly than that of those for the SLS treated skin. These results clearly show that the shower gel formulation made from a surfactant composition of the invention was milder and gentler than the SLS solution when applied to human skin. SLS disrupted the skin's barrier properties, while the shower gel formulation made from a surfactant composition of the invention did not.

Example 4

Comparative Evaluation of Surfactant Mixtures for Irritation Potential with Patch Test A repeat insult patch test (RIPT, see Example 1) was conducted to compare the surfactant compositions of the invention to other skin cleanser products. The surfactant mixture formulations that were tested are shown below in Table 2.

TABLE 2

Formulas for Experimental Test Formulas A and B

| | Percentage (w/w) | | |
| --- | --- | --- | --- |
| Ingredients | Enfuselle ® Moisturizing Shower Gel | Experimental Formula A | Experimental Formula B |
| Water | 25.4846 | 29.6500 | 29.1500 |
| Sodium Lauryl Sulfoacetate and Disodium Laureth Sulfoacetate | 29.0000 | 29.0000 | 29.0000 |
| Ammonium Laureth Sulfate | 24.0000 | 24.0000 | 24.0000 |
| Cocamidopropyl Betaine | 16.0000 | 16.0000 | 16.0000 |
| Coco-Glucoside and Coconut Oil | 1.3500 | 1.3500 | 1.3500 |
| Benzyl Alcohol | 0.9500 | — | — |
| Coco Phosphatidyl PG-Dimonium Chloride | 0.5000 | — | 0.5000 |
| Glycol Distearate | 0.5000 | — | — |
| Fragrance | 0.4500 | — | — |
| Panthenol, 50% in Water | 0.4000 | — | — |
| Dimethicone Copolyol | 0.2000 | — | — |

TABLE 2-continued

Formulas for Experimental Test Formulas A and B

| | Percentage (w/w) | | |
|---|---|---|---|
| Ingredients | Enfuselle ® Moisturizing Shower Gel | Experimental Formula A | Experimental Formula B |
| Methylparaben | 0.2000 | — | — |
| Sodium Benzoate | 0.2000 | — | — |
| Sodium Polyasparte | 0.1000 | — | — |
| Sodium Methyl Cocoyl Taurate | 0.1000 | — | — |
| Tocopheryl Acetate | 0.1000 | — | — |
| Propylparaben | 0.1000 | — | — |
| Disodium EDTA | 0.1000 | — | — |
| Butylene Glycol, Water, and Algae Extract | 0.1000 | — | — |
| Beta Glucan | 0.1000 | — | — |
| Butylparaben | 0.0500 | — | — |
| Sea Water | 0.0100 | — | — |
| Magnesium Ascorbyl Phosphate | 0.0040 | — | — |
| Retinyl Palmitate and Tocopherol | 0.0005 | — | — |
| Grape Seed Extract | 0.0005 | — | — |
| Superoxide Dismutase | 0.0004 | — | — |
| Total | 100.0000 | 100.0000 | 100.0000 |

These formulations were tested relative to cleanser products that are currently on the market. Since the exact formulations for the cleanser products tested are the trade secret of their respective manufacturers, the information listed in Table 3 only shows the ingredients contained in those formulations as described in the cosmetic ingredient declarations found on the packages of these marketed products.

TABLE 3

Ingredient Listing of Products Tested for Comparison Analysis

| Competitive Product | Ingredient Listing |
|---|---|
| Lancome Tresor Perfumed Bath And Shower Gel (Lancome, Inc.) | Water, TEA Lauryl Sulfate, Sodium Laureth Sulfate, Fragrance, Polysorbate 20, Cocamidopropyl Betaine, Acrylate/Steareth-20 Methacrylate Copolymer, Cocamide MEA, Phenoxyethanol, Benzophenone-4, Methylparaben, Propylparaben, Sodium Hydroxide, Triethanolamine, Polyquaternium-7, Propylene Glycol, Disodium EDTA, Aloe Barbadensis (*Aloe Barbadensis*) Gel, Bisabolol, Triclosan, Sea Rocket (*Cakile Maritima*) Extract, Algae (Algae) Extract, Glycerin, Crithmum Maritimum (*Crithmum Maritimum*) Extract, Pacific Sea Kelp (*Macrocystis Pyrifera*) Extract, FD&C Red No. 4, D&C Yellow No. 10 |
| Estee Lauder Beautiful Bath and Shower Gelee (Estee Lauder) | Purified Water, Sodium Laureth Sulfate, Lauramide DEA, Lauramidopropyl Betaine, Fragrance, Sodium Phosphate, Linoleamide DEA, PEG-20 Methyl Glucose Sesquistearate, Tocopheryl Acetate, TEA Lauryl Sulfate, Sodium Lauryl Sulfate, Methylcellulose, Isopropyl Alcohol, Disodium Phosphate, Sodium Chloride, Butylene Glycol, Disodium EDTA, Sodium Metabisulfate, Methylparaben, Ethylparaben, Propylparaben, Potassium Sorbate, Guanine, FD&C Red No. 4, Ext. D&C Violet No. 2 |
| Liz Claiborne Bath and Shower Gel (Liz Claiborne Cosmetics) | Water, TEA Lauryl Sulfate, Sodium Laureth Sulfate, Cocamidopropyl Betaine, PEG-40 Hydrogenated Castor Oil, Aloe Vera (*Aloe Barbadensis*) Gel, Fragrance, PEG-150 Pentaerythrityl Tetrastearate, Lauramide DEA, Glycerin, Oat Beta Glucan, Propylene Glycol, Grape Seed Oil, Benzophenone-4, Disodium EDTA, Diazolidinyl Urea, Methylparaben, Propylparaben, BHT, FD&C Yellow No. 6, FD&C Yellow No. 5 |

TABLE 3-continued

Ingredient Listing of Products Tested for Comparison Analysis

| Competitive Product | Ingredient Listing |
|---|---|
| Neutrogena Rainbath Moisture Rich Shower and Bath Gel (Neutrogena Corp.) | Purified Water, Sodium Laureth Sulfate, Cocamidopropyl Betaine, Glycerin, Sodium Cocoyl Isethionate, Sodium Methyl Cocoyl Taurate, Disodium Cocoamphodiacetate, Polyquaternium-7, Linoleamidopropyl PG-Dimonium Chloride Phosphate, Isostearamidopropyl Laurylacetodimonium Chloride, Aloe Extract, Panthenol, Methylparaben, DMDM Hydantion, Ethylparaben, Tetrasodium EDTA, E&C Green No. 5, Caramel, Fragrance |

Sixty-two test subjects were enrolled in this test. Ten (10) subjects did not complete the test for reasons unrelated to the test itself or the products tested. Therefore, the results were obtained for the 52 test subjects who completed the test procedure.

There were 9 patches applied during the induction phase and 1 patch applied during the challenge phase (see Example 1). The data shown in Table 4 shows the total percentage of test subjects experiencing reactions during these two test phases.

TABLE 4

Percentage of Test Subjects Experiencing Reactions

| Product/Formulation | Only During Induction Phase | Only During Challenge Phase | During Both Phases | Total Number of Reactors |
|---|---|---|---|---|
| Lancome Tresor Perfumed Bath and Shower Gel | 34 | 0 | 5 | 39 |
| Estee Lauder Beautiful Bath and Shower Gelee | 30 | 1 | 7 | 38 |
| Liz Claiborne Sport Bath and Shower Body Gel | 32 | 2 | 4 | 38 |
| Neutrogena Rainbath Moisture Rich Shower and Bath Gel | 26 | 1 | 2 | 29 |
| Enfuselle ® Moisturizing Shower Gel | 22 | 0 | 4 | 26 |
| Experimental Formula B | 18 | 4 | 5 | 27 |
| Experimental Formula A | 18 | 0 | 2 | 21 |

The Enfuselle® Moisturizing Shower Gel and the two additional formulations (Experimental Formulas A and B) exhibited the lowest reaction rate of any of the products/formulations tested. This is true except for the challenge phase on Experimental Formula B. However, it is important to note that all of the reactions observed for Experimental Formula B were "+" reactions (barely perceptible erythema (see Example 1)), which are the most minimal reaction observable according to the evaluation system used in this test.

The data presented in Table 5 demonstrates the total number of reactions found during both phases of the test. The number of reactions observed for the Enfuselle® Moisturizing Shower Gel and formulations A and B were lower than any of the competitive skin cleansing products tested.

TABLE 5

Results of RIPT[a]

| Product or Formulation | Number of of + Graded Sites Found | Number of 1 Graded Sites Found | Number of 2 Graded Sites Found | Total Number of Reactions Found[c] |
|---|---|---|---|---|
| Lancome Tresor Perfumed Bath and Shower Gel | 160 | 29 | 1 | 190 |
| Estee Lauder Beautiful Bath and Shower Gelee | 117 | 36 | 3 | 156 |
| Liz Claiborne Sport Bath and Shower Body Gel | 129 | 29 | 0 | 158 |
| Neutrogena Rainbath Moisture Rich Shower and Bath Gel | 99 | 12 | 0 | 111 |
| Enfuselle ® Moisturizing Shower Gel | 91 | 10 | 2 | 103 |
| Experimental Formula B | 77 | 9 | 0 | 86 |
| Experimental Formula A | 72 | 5 | 0 | 77 |

[a]The results presented are for both the induction and challenge phases of this test.
[b]The grading scale for irritation employed in this test is as follows:
+—Barely perceptible erythema (minimal, faint, uniform or spotty redness)
1—Mild erythema (pink, uniform redness covering most of the test site)
2—Moderate erythema (marked redness visible uniform throughout the test site)
3—Severe erythema (definite bright redness with or without petechiae or papules)
4—Very severe erythema (deep redness with or without vesiculation or weeping)
[b]No irritation greater than a grade 2 was found for any of the samples tested.

When the results from only the induction phase were analyzed, the data clearly indicated that the Enfuselle® Moisturizing Shower Gel and formulations A and B are milder than those of the related products. The same trend was found for the results of the challenge phase, although some reactions were noted for Experimental Formula B. However, as noted above, all of the reactions observed for Formula B were "+" reactions. These are the least severe reactions observable and were comparable in number (but not servity) to the reactions found for the Estee Lauder Beautiful Bath and Shower Gelee and Liz Claiborne Sport Bath and Shower Gel.

Based upon these results, the Enfuselle® Moisturizing Shower Gel and component formulations A and B have been demonstrated to be very mild to the skin. Clearly, these formulations are milder to the skin than skin cleanser products found in the currently marketed products. The results clearly demonstrates that the Enfuselle® Moisturizing Shower Gel and Formulations A and B are unique among skin cleanser formulations in terms of their gentleness to the skin. According to the data presented, that uniqueness is a result of the specific combination of cleansing agents used in these formulations.

Example 5

Comparative Evaluation of Skin Moisture Content Following Application to the Skin Results of the effect of skin cleanser preparations on the moisture levels of the skin are shown in Example 3. The Enfuselle® Moisturizing Shower Gel and Formulas A and B (see Table 2) were compared to several related products (see Table 3) using the measurement of moisture content of human skin described in Example 3.

The results in Table 6 show the moisture content intact human skin resulting from the application of these competitive skin cleanser products and the Enfuselle® Moisturing Shower Gel component formulations (Experimental Formulas A and B) as well as a control site that was only treated with warm water.

TABLE 6

Moisture Content of Skin Following Application of Skin Cleanser

| Time of Evaluation (Hrs)[a] | Control | Estee Lauder Beautiful | Lancome Tressor | Claiborne Sport | Neutrogena Rainbath | Formula A | Formula B |
|---|---|---|---|---|---|---|---|
| 0.0 | 204.4 | 203.1 | 204.1 | 204.3 | 203.8 | 204.5 | 204.5 |
| 1.0 | 189.7 | 172.0 | 162.1 | 162.2 | 172.0 | 181.9 | 181.1 |
| 2.0 | 196.4 | 182.9 | 170.3 | 175.0 | 182.0 | 193.0 | 192.8 |
| 4.0 | 202.3 | 192.1 | 186.9 | 189.6 | 192.0 | 200.3 | 200.7 |
| 6.0 | 203.7 | 197.8 | 196.2 | 196.2 | 199.9 | 203.1 | 203.1 |
| 24.0 | 204.1 | 203.8 | 204.5 | 204.3 | 203.8 | 203.8 | 203.6 |

A matched pairs statistical analysis was then conducted for the data shown in Table 6. These statistical comparisons clearly demonstrate that the Enfuselle® Moisturizing Shower Gel and Formulation A and Formulation B have an effect upon skin moisture levels following application to the skin. In fact, even though all of the competitive products and the Enfuselle® Moisturizing Shower Gel component formulations have an effect upon skin moisture levels for the first two (2) hours of the test, Experimental Formula B (which contains all of the cleansing ingredients of the Enfuselle® Moisturizing Shower Gel), has the least effect upon the skin's moisture levels. Furthermore, although the initial results suggested that Experimental Formula A had a greater effect on skin moisture levels than Experimental Formula B, the lower skin moisture levels found for Formula A were not statistically significant.

The only other skin cleanser preparation found to be statistically similar to the untreated skin site (aside from that observed at 24 hours) is the Neutrogena Rainbath Moisture Rich Shower and Bath Gel at the 6 hours observation point. However, the data clearly showed that the skin moisture levels for this product treated site at the 6 hour observation point were lower than that found for either Experimental Formulas A or B. Thus, Experimental Formula A and B demonstrated superior results to even the Rainbath Moisture Rich Shower and Bath Gel.

The data shown in Table 7 are calculated in terms of percentage change from baseline values.

TABLE 7

Percentage Change in the Moisture Content of Skin Following Application of Skin Cleanser[a]

| Time of Evaluation (Hrs)[b] | Control | Estee Lauder Beautiful | Lancome Tressor | Claiborne Sport | Neutrogena Rainbath | Formula A | Formula B |
|---|---|---|---|---|---|---|---|
| 0.0 | 0.00 | 0.00 | 0.00 | 0.00 | 0.00 | 0.00 | 0.00 |
| 1.0 | −7.07 | −15.19 | −20.48 | −20.49 | −15.43 | −10.92 | −11.30 |
| 2.0 | −3.90 | −9.86 | −16.47 | −14.33 | −10.62 | −5.59 | −5.67 |
| 4.0 | −1.00 | −5.31 | −8.29 | −7.16 | −5.63 | −2.02 | −1.86 |
| 6.0 | −0.30 | −2.54 | −2.94 | −3.97 | −1.78 | −0.68 | −0.68 |
| 24.0 | −0.12 | 0.30 | 0.16 | −0.01 | −0.03 | −0.31 | −0.41 |

[a]The reported percentage change in skin moisture content (PCSMC) is the average of the percentage change in skin moisture content (SMC) for all test subjects calculated from the following equation for each test subject at each measurement point:
PCSMC = 100 × [(SMC$_t$ − SMC$_0$)/SMC$_0$]
[b]Time at which the moisture content of the skin was measured using a NOVA ™ Meter. All times were measured from the time of application of the test product except for the initial reading which was made before treating the skin.

These results clearly show the reduced loss of skin moisture for Formulas A and B as compared to other skin cleanser products. This data also shows that the component formulations A and B return to normal skin moisture levels more rapidly than the competitive skin cleanser products. The data shown indicate that the two component formulations (Formulation A and B) are not statistically different from one another. In addition, Formulation A and B are more statistically similar to the data for the control site than any of the other skin cleanser products tested.

These results demonstrate that the surfactant formulations of the invention are very mild to human skin. Since this mildness comes from a combination of conventional skin cleansers, this result is not only unexpected, but is also novel and unique.

In view of the many possible embodiments to which the principles of the invention may be applied, it should be recognized that the illustrated embodiments are examples of the invention, and should not be taken as a limitation on the scope of the invention. Rather, the scope of the invention is defined by the following claims. We therefore claim as our invention all that comes within the scope and spirit of these claims.

We claim:

1. A composition for cleansing, comprising at least 2% of a mixture of a salt of an alkyl sulfoacetate and a salt of an ethoxylated alkyl sulfosuccinate, at least 3% of a salt of an ethoxylated alkyl sulfate, at least 1% of an amphoteric surfactant, at least 0.05% of an alkyl glucoside, and at least 0.005% of a phospholipid.

2. The composition of claim 1, comprising the mixture of a salt of an alkyl sulfoacetate and a salt of an ethoxylated alkyl sulfosuccinate in a concentration of about 2 to 70%.

3. The composition of claim 1, wherein the salt of an alkyl sulfoacetate comprises a C8–C30 alkyl sulfoacetate.

4. The composition of claim 3, wherein the salt of an alkyl sulfoacetate is selected from the group consisting of a monovalent salt, a divalent salt, and a trivalent salt.

5. The composition of claim 4, wherein the monovalent salt is selected from the group consisting of an ammonium, a sodium, a lithium and a potassium salt.

6. The composition of claim 4, wherein the monovalent salt is selected from the group consisting of a monoalkylammonium ion, a dialkylammonium ion, a trialkylammonium ion, a hydroxylated alkyl ammonium ion, a monoethanolammonium ion, a diethanolammonium ion, and a triethanolammonium ion.

7. The composition of claim 4, wherein the divalent salt is selected from the group consisting of a calcium, a magnesium and a barium salt.

8. The composition of claim 1, wherein the salt of an alkyl sulfoacetate is a salt of a lauryl sulfoacetate.

9. The composition of claim 8, wherein the salt of a lauryl sulfoacetate is sodium lauryl sulfoacetate.

10. The composition of claim 1, wherein the salt of an ethoxylated alkyl sulfosuccinate is a C8–C30 ethoxylated alkyl sulfosuccinate.

11. The composition of claim 1, wherein the salt of an ethoxylated alkyl sulfosuccinate is selected from the group consisting of a monovalent salt, a divalent salt, and a trivalent salt.

12. The composition of claim 11, wherein the monovalent salt is selected from the group consisting of a sodium, an amonium, a lithium and a potassium salt.

13. The composition of claim 11, wherein the monovalent salt is selected from the group consisting of a monoalkylammonium ion, a dialkylammonium ion, a trialkylammonium ion, a hydroxylated alkyl ammonium ion, a monoethanolammonium ion, a diethanolammonium ion, and a triethanolammonium ion.

14. The composition of claim 11, wherein the divalent salt is selected from the group consisting of a calcium, a magnesium and a barium salt.

15. The composition of claim 1, wherein the salt of an ethoxylated alkyl sulfosuccinate is disodium laureth sulfosuccinate.

16. The composition of claim 1, comprising the salt of the ethoxylated alkyl sulfate in a concentration of about 3% to 40%.

17. The composition of claim 1, wherein the salt of an ethoxylated alkyl sulfate is selected from the group consisting of a monovalent salt, a divalent salt, and a trivalent salt.

18. The composition of claim 17, wherein the wherein the monovalent salt is selected from the group consisting of an ammonium, a sodium, a lithium and a potassium salt.

19. The composition of claim 17, wherein the monovalent salt is selected from the group consisting of a monoalkylammonium ion, a dialkylammonium ion, a trialkylammonium ion, a hydroxylated alkyl ammonium ion, a monoethanolammonium ion, a diethanolammonium ion, and a triethanolammonium ion.

20. The composition of claim 17, wherein the divalent salt is selected from the group consisting of a calcium, a magnesium and a barium salt.

21. The composition of claim 1, wherein the ethoxylated alkyl sulfate comprises ammonium laureth sulfate.

22. The composition of claim 1, comprising the amphoteric surfactant in a concentration of about 1% to about 40%.

23. The composition of claim 1, wherein the amphoteric surfactant is selected from the group consisting of a betaine, a sultaine, a hydroxysultaine, an imidazoline, an aminoalkanoate, and an iminoalkanoate.

24. The composition of claim 1, wherein the amphoteric surfactant comprises cocamidopropyl betaine.

25. The composition of claim 1, comprising the alkyl glucoside in a concentration of about 0.05% to 10%.

26. The composition of claim 1, wherein the alkyl glucoside comprises a linear alcohol or a branched chain alcohol.

27. The composition of claim 1, wherein the alkyl glucoside comprises a C8–C30 alkyl glucoside.

28. The composition of claim 25, wherein the alkyl glucoside comprises coco-glucoside.

29. The composition of claim 1, comprising the phospholipid in a concentration of about 0.005% to 10%.

30. The composition of claim 1, wherein the phospholipid is selected from the group consisting of Coco Phosphatidyl PG-Dimonium Chloride, Linoleamidopropyl Phosphatidyl PG-Dimonium Chloride, Cocamidopropyl Phosphatidyl PG-Dimonium Chloride, Borageamidopropyl Phosphatidyl PG-Dimonium Chloride, Stearamidopropyl Phosphatidyl PG-Dimonium Chloride, lecithin, and a derivative of lecithin.

31. The composition of claim 1, further comprising a preservative.

32. The composition of claim 31, wherein the preservative is selected from the group consisting of DMDM Hydantion, Imidazolidnyl Urea, Diazolidinyl Urea, Benzyl Alcohol, Coco Phosphatidyl PG-Dimonium Chloride, a paraben, or a salt of ethylenediamine tetraacetate.

33. The composition of claim 1, further comprising less than about 1% ethylene glycol distearate.

34. The composition of claim 1, further comprising a fragrance.

35. The composition of claim 1, further comprising an antioxidant.

36. The composition of claim 35, wherein the antioxidant is selected from the group consisting of a pro-vitamin, a vitamin, a plant extract, an enzyme and an oat derivative.

37. The composition of claim 1, further comprising a skin feel additive.

38. The composition of claim 37, wherein the skin feel additive is selected from the group consisting of a silicone, a taurate, an emollient, and a protein.

39. The composition of claim 1, further comprising an opacifier or a perlescent agent.

40. The composition of claim 39, wherein the opacifier or pearlescent agent is selected from the group consisting of an Ethylene Glycol Distearate, a Propylene Glycol Distearate, a Polyoxypropylene Glycol (POP) Distearate, a Polyoxyethylene Glycol (POE) Distearate, a Polyoxyethylene/Polyoxypropylene (POE/POP) Distearate, a high molecular weight distearate, a high molecular weight fatty acid, and a mica based pearlescent agent.

41. The composition of claim 1, comprising the salt of the ethoxylated alkyl sulfosuccinate and the salt of the alkyl sulfoacetate in a ratio of about 0.7:1 to 6.6:1.

42. The composition of claim 1, comprising the salt of the ethoxylated alkyl sulfosuccinate and the salt of the alkyl sulfoacetate in the ratio of about 2.3:1.

43. The composition of claim 1, comprising a ratio of from about 0.05 to about 2.0 of the salt of an ethoxylated alkyl sulfosuccinate, from about 0.05 to about 1.5 of a salt of an alkyl sulfoacetate, from about 0.1 to about 2.0 of a salt of an ethoxylated alkyl sulfate, from about 0.05 to about 3.0 of an amphoteric surfactant, from about 0.005 to about 1.0 of an alkyl glucoside, and from about 0.0005 to about 0.5 of a phospholipid.

44. The composition of claim 1, wherein:
   (a) a ratio of the phospholipid to the salt of the ethoxylated alkyl sulfosuccinate is from about 1:10 to about 1:44; or
   (b) a ratio of the phospholipid to the salt of the alkyl sulfoacetate is from about 1:1 to about 1:22; or
   (c) a ratio of the phospholipid to the salt of an ethoxylated alkyl sulfate is from about 1:15 to about 1:60; or
   (d) a ratio of the phospholipid to the amphoteric surfactant is from about 1:10 to about 1:40; or
   (e) a ratio of the phospholipid to the alkyl glucoside is from about 1:0.5 to about 1:15.

45. The composition of claim 1, wherein:
   (a) a ratio of the phospholipid to the salt of the ethoxylated alkyl sulfosuccinate is from about 1:20 to about 1:34;
   (b) a ratio of the phospholipid to the salt of the alkyl sulfoacetate is from about 1:8 to about 1:15;
   (c) a ratio of the phospholipid to the salt of the ethoxylated alkyl sulfate is from about 1:25 to about 1:50;
   (d) a ratio of the phospholipid to the amphoteric surfactant is from about 1:20 to about 1:30; or
   (e) a ratio of the phospholipid to the alkyl glucoside is from about 1:2 to about 1:12.

46. The composition of claim 1, wherein:
   (a) a ratio of the phospholipid to the salt of the ethoxylated alkyl sulfosuccinate is about 1:27; or
   (b) a ratio of the phospholipid to the salt of the alkyl sulfoacetate is about 1:12; or
   (c) a ratio of the phospholipid to the salt of the ethoxylated alkyl sulfate is about 1:38; or
   (d) a ratio of the phospholipid to the amphoteric surfactant is about 1:25; or
   (e) a ratio of the phospholipid to the alkyl glucoside is about 1:7.

47. A cleansing composition, comprising:
   (a) about 2% to 70% of a mixture of a salt of an alkyl sulfoacetate and a salt of an ethoxylated alkyl sulfosuccinate;

(b) about 3% to 40% of a salt of an ethoxylated alkyl sulfate;

(c) about 1% to 40% of an amphoteric surfactant;

(d) about 0.05% to 10% of an alkyl glucoside; and (e) about 0.005% to 10% of a phospholipid.

48. The composition of claim 46, wherein the salt of the alkyl sulfoacetate comprises a salt of lauryl sulfoacetate.

49. The composition of claim 46, wherein the salt of the ethoxylated alkyl sulfosuccinate comprises a salt of laureth sulfosuccinate.

50. A composition for cleaning, comprising:
   (a) about 41% of a mixture of alkyl sulfoacetate and ethoxylated alkyl sulfosuccinate;
   (b) about 34% of an ethoxylated alkyl sulfate;
   (c) about 22% of a amphoteric surfactant;
   (d) about 2% of a alkyl glucoside; and
   (e) about 1% of a phospholipid.

51. A diluted composition for cleansing, comprising about 0.5% to 95% of the composition of claim 1.

52. A composition for cleansing, comprising about 2% to 50% of a mixture of a salt of a sodium lauryl sulfoacetate and Disodium Laureth Sulfosuccinate, about 3% to 35% of Ammonium Laureth Sulfate, about 1% to 30% of Cocamidopropyl Betaine, about 0.05% to 8% of Coco-Glucoside and Coconut Oil, and about 0.005% to 5% of a phospholipid.

53. The composition of claim 52, comprising about 5% to 40% of a mixture of a salt of a sodium lauryl sulfoacetate and Disodium Laureth Sulfosuccinate, about 5% to 30% of Ammonium Laureth Sulfate, about 3% to 20% of Cocamidopropyl Betaine, about 0.5% to 5% of Coco-Glucoside and Coconut Oil, and about 0.05% to 3% of a phospholipid.

54. A composition for cleansing, comprising about 29% Sodium Lauryl Sulfoacetate and Disodium Laureth Sulfosuccinate, 39% Water, 24% Ammonium Laureth Sulfate, 16% Cocamidopropyl Betaine, 1% Coco-Glucoside and Coconut Oil, and 0.05% Coco Phosphatidyl PG-Dimonium Chloride.

55. A method for cleansing, comprising contacting a sufficiently cleansing amount of the composition of claim 1 with a surface to be cleaned.

56. The method of claim 55, wherein the surface is selected from the group consisting of a hard surface, a porous surface, a skin surface, a hair, a fabric and a mucous membrane.

\* \* \* \* \*